United States Patent
Schloss

(12) 
(10) Patent No.: US 6,539,260 B1
(45) Date of Patent: Mar. 25, 2003

(54) ATRIAL SENSING AND PACING USING A UNIPOLAR ATRIAL ELECTRODE

(75) Inventor: Harold C. Schloss, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/514,631

(22) Filed: Feb. 28, 2000

(51) Int. Cl.[7] ............................................. A61N 1/362
(52) U.S. Cl. ................................................. 607/9; 607/4
(58) Field of Search ................................. 607/122, 123, 607/119, 9, 4, 15; 600/509

(56) References Cited

U.S. PATENT DOCUMENTS

| | | | |
|---|---|---|---|
| 4,712,555 A | 12/1987 | Thornander et al. | 128/419 |
| 4,774,952 A | 10/1988 | Smits | 128/419 |
| 4,788,980 A | 12/1988 | Mann et al. | 128/419 |
| 4,809,697 A | 3/1989 | Causey, III et al. | 128/419 |
| 4,940,052 A | 7/1990 | Mann et al. | 128/419 |
| 4,944,298 A | 7/1990 | Sholder | 128/419 |
| 4,944,299 A | 7/1990 | Silvian | 128/419 |
| 4,991,603 A | 2/1991 | Cohen et al. | 128/786 |
| 4,998,975 A | 3/1991 | Cohen et al. | 128/419 |
| 5,522,855 A | 6/1996 | Hoegnelid | 607/9 |
| 5,534,022 A * | 7/1996 | Hoffmann et al. | 607/119 |
| 5,571,143 A | 11/1996 | Hoegnelid et al. | 607/9 |
| 5,571,163 A | 11/1996 | Helland | 607/123 |
| 5,720,768 A * | 2/1998 | Verboven-Nelissen | 607/9 |
| 5,782,898 A * | 7/1998 | Dahl et al. | 600/374 |
| 5,800,465 A * | 9/1998 | Thompson et al. | 607/122 |
| 5,814,076 A * | 9/1998 | Brownlee | 128/901 |
| 5,814,079 A * | 9/1998 | Kieval | 607/14 |
| 6,345,198 B1 * | 2/2002 | Mouchawar et al. | 600/374 |
| 6,430,449 B1 * | 8/2002 | Hsu et al. | 607/126 |

\* cited by examiner

*Primary Examiner*—Kennedy Schaetzle

(57) ABSTRACT

A system and method for performing bipolar sensing and pacing in a heart using a unipolar atrial electrode. The invention provides a lead system comprising an atrial electrode placed in the atrium of the heart and a defibrillation electrode placed in the heart. The defibrillation electrode may be placed in the ventricle, the superior vena cava, or the coronary sinus. Bipolar pacing and sensing in the atrium is achieved without the introduction of additional conductors into the atrium.

12 Claims, 7 Drawing Sheets

| CONFIGURATION | ANODE (POSITIVE) | THRESHOLD (V) | LOCATION |
|---|---|---|---|
| ATIP TO DEFIB. ELECTRODE | DEFIB. ELECTRODE | >10 | VENTRICLE |
| | | 0.6 | ATRIUM |
| ATIP TO DEFIB. ELECTRODE | ATIP | >10 | VENTRICLE |
| | | 0.6* | ATRIUM |
| ATIP TO VTIP | ATIP | 0.7 | ATRIUM |
| ATIP TO VTIP | VTIP | 2.1 | VENTRICLE |
| ATRIAL BIPOLAR | ARING | 0.6 | ATRIUM |
| ARING TO DEFIB. ELECTRODE | ARING | 3.5 | VENTRICLE |
| ARING TO DEFIB. ELECTRODE | DEFIB. ELECTRODE | 6.0 | VENTRICLE |

* ESTIMATED (NOT AN ACTUAL MEASUREMENT)

FIG. 6

| CONFIGURATION | ANODE (POSITIVE) | P-WAVE (mV) | R-WAVE (mV) |
|---|---|---|---|
| ATIP TO VTIP | VTIP | 8.0 | 25.0 |
| ATIP TO DEFIB. ELECTRODE | DEFIB. ELECTRODE | 8.0 | 11.0 |
| ARING TO VTIP | VTIP | 1.5 | 24.0 |
| ARING TO DEFIB. ELECTRODE | DEFIB. ELECTRODE | 1.7 | 12.0 |

FIG. 7

ATRIAL SENSING AND PACING USING A UNIPOLAR ATRIAL ELECTRODE

FIELD OF THE INVENTION

The invention relates generally to implantable medical devices, such as cardiac pacemakers, cardioverters and defibrillators. More particularly, this invention relates to lead systems employed for pacing, cardioverting or defibrillating a heart.

DESCRIPTION OF THE RELATED ART

Implantable stimulation devices (ISDs), such as cardiac pacemakers, are often used to remedy improper heart function. These devices generally provide an electrical pulse to a selected area of the heart that is not (in terms of timing or strength) adequately receiving its natural pulse. Under abnormal cardiac conditions, and particularly cardiac rhythm disturbances, pacemaker therapy is applied to remedy several forms of cardiac arrhythmias (rhythm disturbances) including bradycardias, AV conduction block, supraventricular tachycardias, and atrial and ventricular ectopic arrhythmias.

There are essentially two kinds of pacemakers: single-chamber and dual-chamber. A single-chamber pacemaker is capable of sensing and pacing in only one of the atrium or the ventricle. From a practical standpoint, there are essentially two forms of single-chamber pacing: VVI (senses and paces in the ventricle) and AAI (senses and paces in the atrium).

A dual-chamber pacemaker is capable of sensing and pacing in both the atrium and the ventricle. There are many modes of dual-chamber pacing such as VDD (paces in the ventricle only, senses in the atrium and ventricle), DVI (paces in the atrium and ventricle, and senses in the ventricle only), DDI (senses and paces in both the atrium and ventricle), and DDD (senses and paces in both the atrium and ventricle, with an inhibited and triggered response to sensing).

A letter "R" is sometimes added to these pacemaker modes to indicate the pacemaker's ability to provide rate-modulated (also sometimes called rate-responsive or rate-adaptive) pacing in response to input from an independent sensor. For instance, a DDDR pacemaker is capable of adapting to the need to increase a patient's heart rate in response to physiologic stress in the absence of intrinsic response from a patient's sinus node.

A pacemaker uses a lead system to perform its sensing and stimulation functions. A lead system typically comprises at least one lead, one or more conductor coils, and one or more electrodes. The lead is the insulated wire used to connect the pulse generator of a pacemaker to the cardiac tissue. The lead carries the output stimulus from the pulse generator to the heart and, in demand modes, relays intrinsic cardiac signals back to the sensing circuitry of the pacemaker. Typically, a single-chamber pacemaker requires one lead, whereas a dual-chamber pacemaker requires two leads (one for the atrium and another for the ventricle). The conductor coil is the internal core of the pacing lead through which current flows between the pulse generator and the electrodes.

A lead may be unipolar or bipolar. A unipolar lead is a pacing lead having one electrical pole external to the pulse generator, which is usually located in the heart. The unipolar lead has one conductor coil. The electrical pole is typically a stimulating cathode (i.e., negative pole) at the distal tip of the lead. As used herein, a distal end of the lead is the end which is farther away from the pacemaker. A proximal end of the lead is the end which is connects to the pacemaker. The cathode is the electrode through which a stimulating pulse is delivered. The anode (i.e., positive pole) is typically attached to the case, or housing, of the pacemaker. A stimulating pulse returns to the anode using the body tissue as a return current path. A unipolar lead is relatively small in size and is theoretically more reliable than a bipolar lead. However, a unipolar lead/pacing system is more susceptible to interference by other electrical activity in a patient's body, such as inhibition due to myopotentials, and further may be prone to pectoral stimulation.

On the other hand, a bipolar lead is a pacing lead with two electrical poles that are external to the pulse generator. The bipolar lead has two conductor coils. The stimulating cathode is typically at the distal tip of the pacing lead, while the anode is an annular (i.e., ring) electrode which is few millimeters proximal to the cathode. As such, bipolar leads are less prone to pectoral stimulation. A bipolar lead has better signal-to-noise ratio than that of a unipolar lead, and thus, is less susceptible to interference from myopotential inhibition.

In practice, the cathode (i.e., stimulating) electrode is typically placed in contact with the heart tissue in order to stimulate the cardiac tissue. The anode electrode, however, does not need to be in contact with the heart tissue, since blood tends to conduct electrical currents better than the tissue itself. Nonetheless, it is preferable to have the sensing electrode in contact with the heart tissue to allow the detection of more distinct signals. As used herein, the terms "cathode" and "anode" are relative by definition. An anode electrode is one which is more positive than a cathode electrode. A cathode electrode is one which is more negative than an anode electrode. For more details on bipolar lead structure and electrode placement, reference is made to commonly-assigned U.S. Pat. No. 5,522,855 (Hoegnelid), issued Jun. 4, 1996, and is incorporated herein in its entirety by reference.

Recently, combination sensing, pacing and defibrillation bipolar ("combipolare") leads were introduced to reduce the number of conductors implanted in the heart. More particularly, a unipolar atrial lead may be used with a ventricular tip electrode (placed in the apex region of the right ventricle) to perform bipolar sensing in the atrium. Atrial signals are often weak. Accordingly, interference from muscular activity typically causes problems in measurements taken in the atrium. Bipolar electrodes have often been used in the atrium in order to minimize the effects of such muscular interference. In this case, with the ventricular tip electrode as the second electrode, there is a substantial possibility of sensing myopotentials greater than that of a standard bipolar atrial electrode. Moreover, atrial pacing is still performed in a unipolar fashion and is, thereby, still susceptible to interference by other electrical activity in a patient's body. For more information on combipolar sensing, reference is made to commonly-assigned U.S. Pat. No. 5,571,143, issued to Hoegnelid et al., and is incorporated herein in its entirety.

Therefore, there is a need in the cardiac pacing technology to sense and pace the atrium using a unipolar lead while maintaining bipolar modality. Such lead structure should minimize the complexity and number of conductors implanted in the heart.

SUMMARY OF THE INVENTION

To overcome the limitations of the prior art, the invention provides a system and method for performing bipolar sensing and pacing in a heart. In one embodiment, the invention provides a lead system which performs bipolar pacing in an atrium of the heart. The lead system comprises an atrial electrode configured for placement in the atrium, and a ventricular electrode configured for placement in the ventricle and having a surface area greater than about 60 mm$^2$. In another embodiment, the lead system comprises an atrial electrode configured for placement in the atrium, and electrically connectable to a pacing circuit. The lead system further comprises a defibrillation electrode configured for placement in the heart, and electrically connectable to the pacing circuit. In another embodiment, the invention provides a lead system which performs bipolar sensing in an atrium of the heart. The lead system comprises an atrial electrode configured for placement in the atrium, and a defibrillation electrode configured for placement in the heart.

Furthermore, the invention provides a method of performing bipolar pacing in an atrium of the heart. The method comprises the steps of delivering pacing signals to the heart via an atrial electrode placed in the atrium, and returning the delivered pacing signals to a pacing circuit via a return electrode having a surface area greater than about 60 mm$^2$. In another embodiment, the method comprises the steps of delivering a pacing signal via an atrial electrode placed in the atrium, and returning the delivered pacing signal via a defibrillation electrode. In another embodiment, the invention provides a method of performing bipolar sensing in an atrium of the heart. The method comprises the steps of sensing an atrial signal via an atrial electrode placed in the atrium, and sensing a cardiac signal via a defibrillation electrode. The method further comprises the step of transferring the sensed signals from the heart to a sensing circuit.

BRIEF DESCRIPTION OF THE DRAWINGS

The above and other aspects, features and advantages of the invention will be better understood by referring to the following detailed description, which should be read in conjunction with the accompanying drawings, in which:

FIG. 6 illustrates a first table summarizing test results for various pacing lead configurations employed to achieve capture in a heart.

FIG. 7 illustrates a second table summarizing test results for various sensing lead configurations employed to sense intrinsic cardiac signals.

DETAILED DESCRIPTION OF THE PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
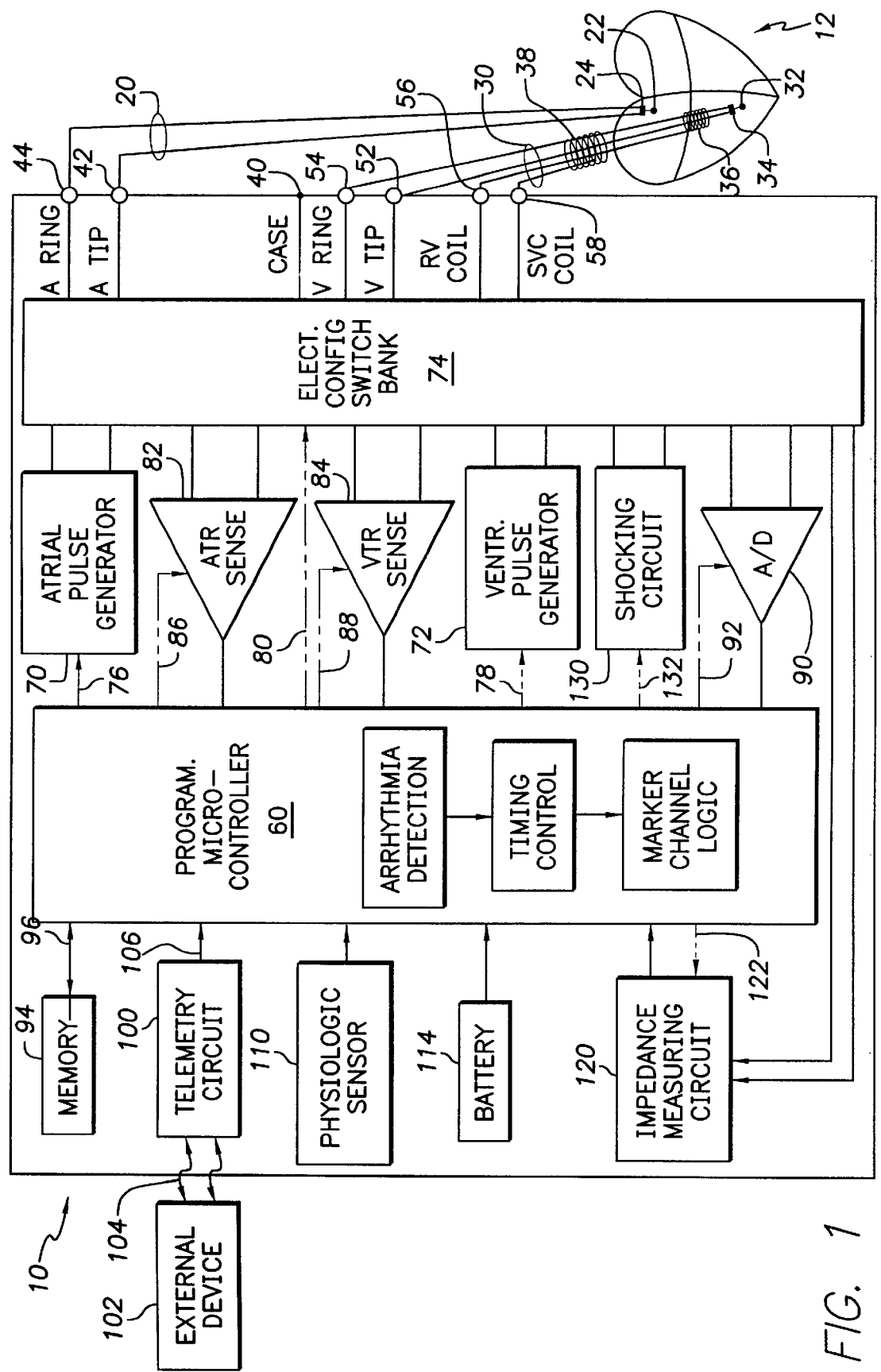
FIG. 1 is a functional block diagram of a dual-chamber implantable stimulation device illustrating the basic elements of a stimulation device which can provide cardioversion, defibrillation and pacing stimulation.

In FIG. 1, a simplified block diagram is shown of a dual-chamber implantable stimulation device 10 which is capable of treating both fast and slow arrhythmias with stimulation therapy, including cardioversion, defibrillation, and pacing stimulation. While a dual-chamber device is shown, this is for illustration purposes only, and one of skill in the art could readily eliminate or disable the appropriate circuitry to provide a single-chamber stimulation device capable of treating one chamber with cardioversion, defibrillation and pacing stimulation.

To provide atrial chamber pacing stimulation and sensing, the stimulation device 10 is shown in electrical communication with a patient's heart 12 by way of an implantable atrial lead 20 having an atrial tip electrode 22 and an atrial ring electrode 24 which typically is implanted in the patient's atrial appendage.

The stimulation device 10 is also shown in electrical communication with the patient's heart 12 by way of an implantable ventricular lead 30 having, in this embodiment, a ventricular tip electrode 32, a ventricular ring electrode 34, a right ventricular (RV) coil electrode 36, and an SVC coil electrode 38. Typically, the ventricular lead 30 is transvenously inserted into the heart 12 so as to place the RV coil electrode 36 in the right ventricular apex, and the SVC coil electrode 38 in the superior vena cava. Accordingly, the ventricular lead 30 is capable of receiving cardiac signals, and delivering stimulation in the form of pacing and shock therapy to the right ventricle.

While only two leads are shown in FIG. 1, it is to be understood that additional stimulation leads (with one or more pacing, sensing and/or shocking electrodes) may be used in order to efficiently and effectively provide pacing stimulation to the left side of the heart or atrial cardioversion and/or defibrillation. For example, a lead designed for placement in the coronary sinus region could be implanted to deliver left atrial pacing, atrial shocking therapy, and/or for left ventricular pacing stimulation. For a complete description of a coronary sinus lead, see U.S. patent application Ser. No. 09/196,898, "A Self-Anchoring Coronary Sinus Lead" (Pianca et. al), and U.S. Pat. No. 5,466,254, "Coronary Sinus Lead with Atrial Sensing Capability" (Helland), which patents are hereby incorporated herein by reference.

The housing 40 (shown schematically) for the stimulation device 10 includes a connector (not shown) having an atrial pin terminal 42 and an atrial ring terminal 44, which are adapted for connection to the atrial tip electrode 22 and the atrial ring electrode 24, respectively. The housing 40 further includes a ventricular pin terminal 52, a ventricular ring terminal 54, a ventricular shocking terminal 56, and an SVC shocking terminal 58, which are adapted for connection to the ventricular tip electrode 32, the ventricular ring electrode 34, the RV coil electrode 36, and the SVC coil electrode 38, respectively. The housing 40 (often referred to as the "can", "case" or "case electrode") may be programmably selected to act as the return electrode, or anode, alone or in combination with one of the coil electrodes, 36 and 38. For convenience, the names of the electrodes are shown next to the terminals.

At the core of the stimulation device 10 is a programmable microcontroller 60 which controls the various modes of stimulation therapy. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art. As shown in FIG. 1, an atrial pulse generator 70 and a ventricular pulse generator 72 generate pacing stimulation pulses for delivery by the atrial lead 20 and the ventricular lead 30, respectively, via a switch bank 74. The pulse generators, 70 and 72, are controlled by the microcontroller 60 via appropriate control signals, 76 and 78, respectively, to trigger or inhibit the stimulation pulses. The microcontroller 60 further includes timing circuitry that controls the operation of the stimulation device timing of such stimulation pulses, that is well known in the art.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches (not shown) as is known in the art. An atrial sense amplifier 82 and a ventricular sense amplifier 84 are also coupled to the atrial and ventricular leads 20 and 30, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82 and 84, preferably employs a low power, precision amplifier with programmable gain and/or automatic gain control, bandpass filtering, and a threshold detection circuit, known in the art, to selectively sense the cardiac signal of interest. The automatic gain control enables the device 10 to deal effectively with the difficult problem of sensing the low frequency, low amplitude signal characteristics of ventricular fibrillation.

The outputs of the atrial and ventricular sense amplifiers, 82 and 84, are connected to the microcontroller 60 which, in turn, inhibit the atrial and ventricular pulse generators, 70 and 72, respectively, in a demand fashion whenever cardiac activity is sensed in the respective chambers.

For arrhythmia detection, the present invention utilizes the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P-P and R-R intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, also known as "tiered therapy").

Cardiac signals are also applied to the inputs of an analog to digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the atrial and ventricular leads, 20 and 30, through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 28 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through the established communication link 104.

In the preferred embodiment, the stimulation device 10 further includes a physiologic sensor 110. Such sensors are commonly called "rate-responsive" sensors. The physiological sensor 110 is used to detect the exercise state of the patient, to which the microcontroller 60 responds by adjusting the rate and AV Delay at which the atrial and ventricular pulse generators, 70 and 72, generate stimulation pulses. The type of sensor used is not critical to the present invention and is shown only for completeness.

The stimulation device additionally includes a battery 114 which provides operating power to all of the circuits shown in FIG. 1. For the stimulation device 10, which employs shocking therapy, the battery must be capable of operating at low current drains for long periods of time, and then be capable of providing high-current pulses (for capacitor charging) when the patient requires a shock pulse. The battery 114 must also have a predictable discharge characteristic so that elective replacement time can be detected. Accordingly, the present invention employs lithium/silver vanadium oxide batteries, as is true for most (if not all) such devices to date.

As further shown in FIG. 1, the present invention preferably includes an impedance measuring circuit 120 which is enabled by the microcontroller 60 by a control signal 122. The impedance measuring circuit 120 is not critical to the present invention and is shown for only completeness.

It is the primary function of the present invention to function as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 130 by way of a control signal 132. The shocking circuit 130 generates shocking pulses of low (up to 0.5 Joules), moderate (0.5–10 Joules), or high energy (11 to 40 Joules), as controlled by the microcontroller 60. Such shocking pulses are applied to the patient's heart through at least two shocking electrodes, and as shown in this embodiment, using the RV and SVC coil electrodes, 36 and 38, respectively. In alternative embodiments, the housing 40 may act as an active electrode in combination with the RV electrode 36 alone, or as part of a split electrical vector using the SVC coil electrode 38 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asychronously (since R-waves may be too disorganized), and pertaining exclusively to the treatment of fibrillation. Accordingly, the microcontroller 60 is capable of controlling the synchronous or asynchronous delivery of the shocking pulses.

Figure 2:
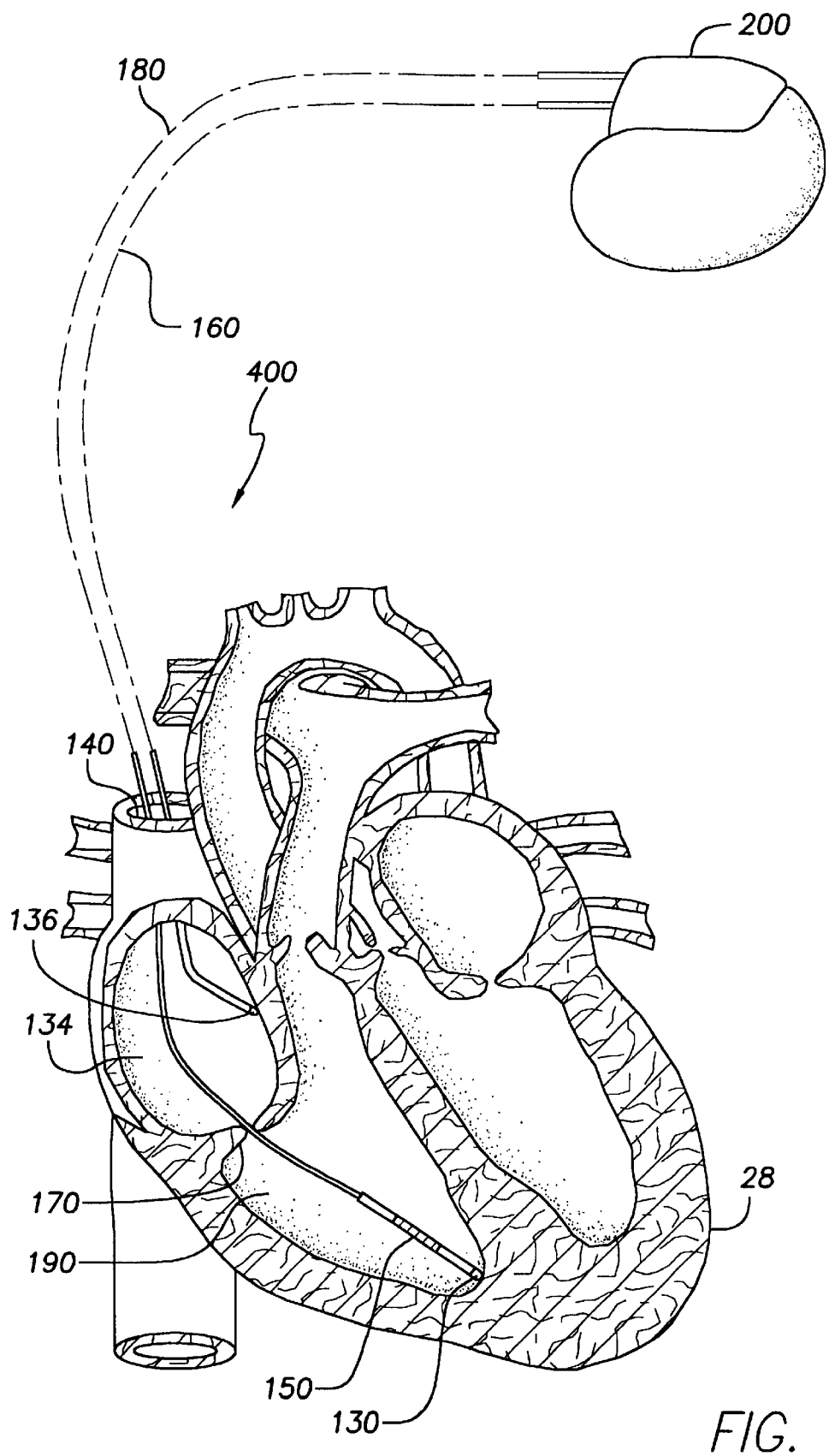
FIG. 2 is a vertical cross-sectional view of a human heart implanted with one embodiment of the lead system of the invention.

FIG. 2 is a vertical cross-sectional view of a human heart 28 implanted with one embodiment of the lead system of the present invention. The lead system 400 may be used with an implantable cardioverter-defibrillator (ICD) or, optionally, with an implantable pacemaker and ICD (collectively an implantable stimulation device or "ISD") 200. The lead system 400 may employ a variety of sensing, pacing and defibrillator leads. One example of such a group of leads is a combination lead having pacing and sensing electrodes, which also includes a defibrillation electrode. For complete design details for such a combination lead, reference is made to the Helland patent (U.S. Pat. No. 5,571,163) which is commonly assigned, and is incorporated in its entirety herein.

In this embodiment, the lead system 400 comprises a ventricular lead 160 and an atrial lead 180. The ventricular lead 160 provides cardioversion-defibrillation and, optionally, bipolar pacing and sensing in the ventricle 190. The lead 160 comprises a defibrillation electrode 150 mounted just proximally of the distal tip in the ventricle 190. The defibrillation electrode 150 may be a coil-type electrode which acts as the cathode, and the housing of the ISD 200 acts as the anode or ground. The ICD 200 provides sufficient energy through the defibrillation electrode 150 to defibrillate the heart 28 and terminate ventricular fibrillation. The lead 160 may also comprise a tip electrode 130 placed in contact with the apex region of the ventricle 190. Bipolar pacing may be performed using the tip electrode 130 as the cathode with the defibrillation electrode 150 as the anode.

The atrial lead 180 is a unipolar lead which, together with an electrode in the ventricle, "combipolar" pacing and sensing in the atrium 134. The atrial lead 180 includes a tip electrode 136 as one of the electrodes needed for performing bipolar sensing and pacing in the atrium 134. For pacing in the atrium 134, the ISD 200 uses the tip electrode 136 as the cathode, and the defibrillation electrode 150 as the anode. For sensing in the atrium 134, the ISD 200 uses the tip electrode 136 and the defibrillation electrode 150 to sense and measure a differential signal between the two electrodes.

Typically, the defibrillation electrode 150 has a relatively large surface area, ranging from 60 to 1000 square millimeters ($mm^2$) or more.

It is preferable, however, that the surface area of the defibrillation electrode 150 be between 100 and 800 $mm^2$. More importantly, the distance between the defibrillation electrode 150 and the atrial tip electrode 136 is less than the distance between the ventricular tip electrode 130 and the atrial tip electrode 136. The relatively large surface area of the defibrillation electrode 150 provides more reliable sensing in the atrium 134. The closer proximity of the defibrillation electrode 150 to the atrial tip electrode 136 reduces signal distortions which may result from interfering myopotentials. Thus, with the unipolar lead 180, the ISD 200 achieves effective bipolar sensing and pacing in the atrium 134 using an already existing second electrode (i.e., the defibrillation electrode 150), and without introducing more conductors into the heart 28.

The defibrillation electrode 150 may be placed in any location where defibrillation is desired and feasible in the heart. Hence, the location of the defibrillation electrode 150 is not limited to placement in the ventricle 190. For instance, the defibrillation electrode 150 may be placed in the superior vena cava (SVC) 140. Alternatively, the defibrillation electrode 150 may be placed in the coronary sinus. Therefore, the placement of the defibrillation electrode 150 in any region of the heart where defibrillation is desired is within the scope of the invention.

Alternatively, tip electrode 136 could be placed in either the coronary sinus or one of the cardiac veins in the heart 28. This arrangement would allow the preferential pacing of either the right atrium, the left atrium, or even the left ventricle of heart 28, depending on the placement of the tip electrode 136. The chamber that is paced would be determined by the exact placement of tip electrode 136 within heart 28. Furthermore, it is contemplated that in another alternative arrangement, a smaller electrode could be substituted for defibrillation electrode 150. This alternative electrode would still need to be substantially larger than tip electrode 136, but this arrangement would allow for bipolar pacing between tip electrode 136 and the alternative electrode. By proper selection of the pacing energy, this would achieve capture of the chamber nearest to tip electrode 136, but not of the chamber nearest to the alternative electrode. It is believed that this alternative electrode would need to be at least four times the surface area of tip electrode 136. In addition, the alternative electrode could be instead a patch electrode, such as electrodes 38 or 40 of FIG. 1.

Figure 3:
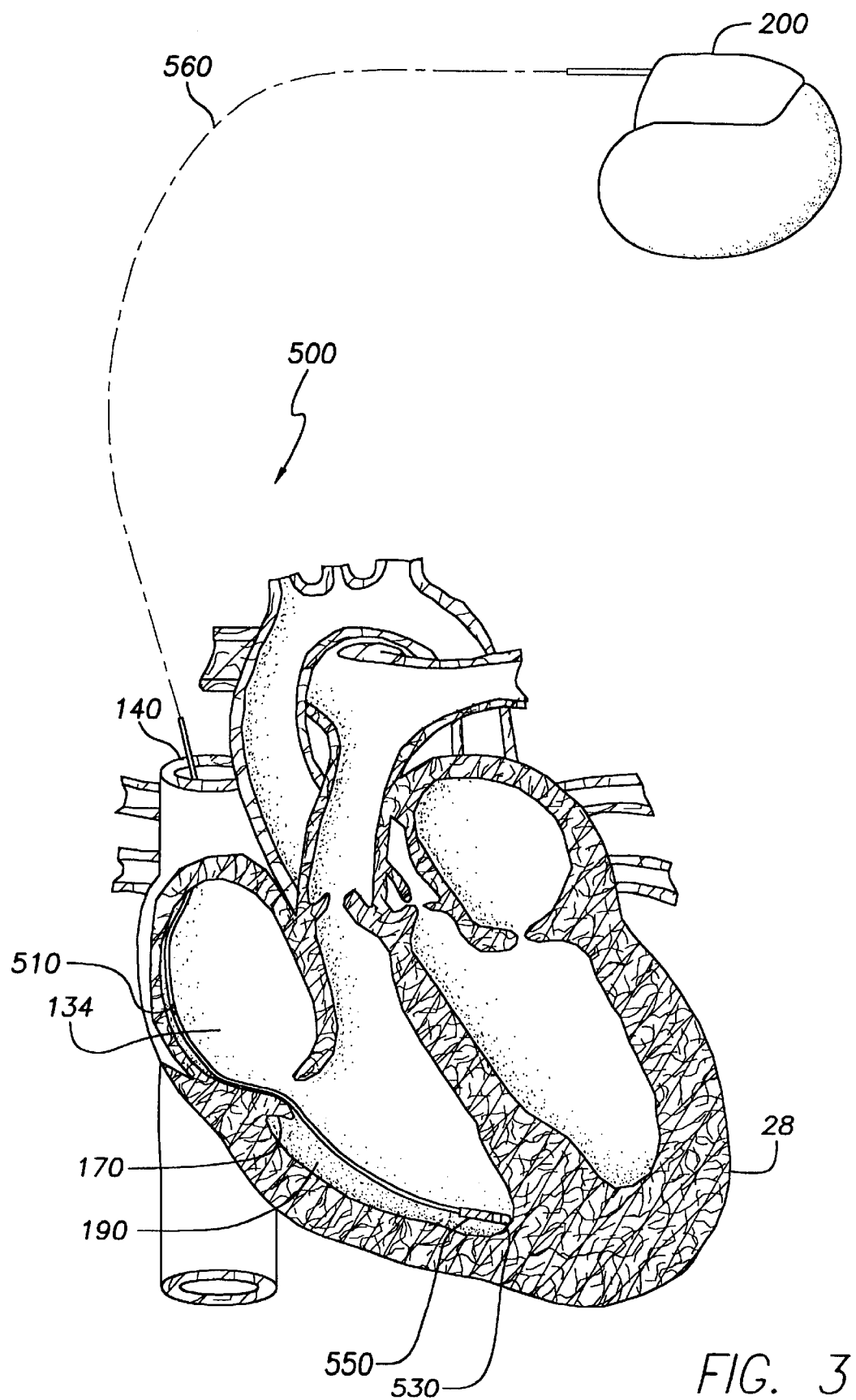
FIG. 3 is a vertical cross-sectional view of a human heart implanted with another embodiment of the lead system of the invention.

FIG. 3 is a vertical cross-sectional view of a human heart 28 implanted with another embodiment of the lead system of the present invention. In this embodiment, the lead system 500 comprises a ventricular lead 560 which includes a tip electrode 530 and a defibrillation electrode 550. The lead system 500 further comprises an atrial ring electrode 510 incorporated with the ventricular lead 560. The ISD 200 may perform unipolar or bipolar pacing, sensing, and cardioversion-defibrillation in the ventricle 190. To perform unipolar pacing, the ISD 200 may employ the tip electrode 530 as the cathode, and the case of the ISD 200 as the anode. To perform bipolar pacing, the ISD 200 may employ the tip electrode 530 as the cathode, and the defibrillation electrode 550 as the anode. To perform cardioversion-defibrillation, the ISD 200 may employ the defibrillation electrode 550 as the cathode, and the case of the ISD 200 as the anode.

Moreover, the ISD 200 performs bipolar sensing and pacing in the atrium 134. To perform bipolar sensing, the ISD 200 employs the defibrillation electrode 550 and the atrial ring electrode 510 to sense and measure the differential signal between these electrodes. To perform bipolar pacing, the ISD 200 employs the atrial ring electrode 510 as the cathode which is placed in contact with, or substantially close proximity to, the walls of the atrium 134. The ISD 200 may employ the defibrillation electrode 550 as the anode to complete the circuit for the pacing signals. Hence, by using the defibrillation electrode 550, the ISD 200 performs bipolar pacing and sensing in the atrium 134 without introducing more conductors (e.g., a second electrode in the atrium 134) into the heart 28.

Upon application of the stimulation pulse between ring electrode 510 and defibrillation electrode 550, current flows therebetween with the current density at the electrode surface being dependent upon the surface area of the electrode. Accordingly, the current density will be relatively higher around the ring electrode 510 than the defibrillation electrode 550, since the surface area of electrode 550 is relatively larger than that of electrode 510. Typically, the surface area for a ring electrode is in the range of 30–40 mm$^2$ and typically the surface area of a tip electrode is about 5 mm$^2$. Thus, the ratio of a ring electrode surface area to tip electrode surface area is in the range of about 6:1. Accordingly, and inasmuch as, both the tip and ring electrodes are considerably smaller than a defibrillation electrode, the atrium only will undergo capture, when a stimulation pulse is applied between the defibrillation electrode and either the tip electrode or ring electrode.

Test results were obtained using the atrial tip electrode 136 and the ventricular defibrillation electrode 150 in atrial bipolar pacing. These test results show a significant improvement over the use of the atrial tip electrode 136 and the ventricular tip electrode 130 in atrial bipolar pacing. FIG. 6 illustrates a first table summarizing test results for various pacing lead configurations employed to achieve capture in the heart 28. The first column 610 indicates the lead configuration used for a particular measurement. The second column 620 indicates which electrode is used as an anode for the particular measurement. The third column 630 indicates the voltage level at which capture is achieved. The fourth column 640 indicates the location of the region of the heart 28 being paced.

As shown in FIG. 6, using the atrial tip electrode 136 as the cathode and the defibrillation electrode 150 as the anode (i.e., Atip to Defib. Electrode configuration), a threshold voltage of 0.6 Volts is needed to achieve capture in the atrium 134. Whereas, using the atrial tip electrode 136 as the cathode and the ventricular tip electrode 130 as the anode (i.e., Atip to Vtip), a threshold voltage of 0.7 Volts is needed to achieve capture in the atrium 134. Hence, when using the defibrillation electrode 150 as the second electrode, a smaller threshold voltage is needed to achieve capture in the atrium 134. Applying a smaller voltage to a heart indicates the use of less energy, thereby enhancing the longevity of the power source (e.g., battery). More importantly, any damage to heart tissue is minimized with the application of a smaller voltage.

Moreover, when using the atrial tip electrode 136 and the defibrillation electrode 150, a threshold voltage greater than 10 Volts is necessary to achieve capture in the ventricle 190. On the other hand, when using the atrial tip electrode 136 and the defibrillation electrode 150, a threshold voltage of only 2.1 Volts is needed to achieve capture in the ventricle 190. With the defibrillation electrode 150 as the second electrode, the voltage needed to achieve capture in the ventricle 190 (i.e., 10 Volts) is greater than when using the ventricular tip electrode 130 as the second electrode (i.e., 2.1 Volts). With the defibrillation electrode 150, the difference in threshold voltages between achieving capture in the atrium 134 and ventricle 190 is greater (i.e., 10−0.6=9.4 Volts) than the difference in threshold voltages when using the ventricular tip electrode 130 (i.e., 2.1−0.7=1.4 Volts). Accordingly, with the defibrillation electrode 150, a much greater voltage is needed to achieve capture in the ventricle 190 than that needed to achieve capture in the atrium 134. Hence, an unintended or accidental capture in the ventricle 190 is less likely when trying to achieve capture in the atrium 134 using the defibrillation electrode 150 as the second electrode.

Furthermore, using conventional atrial bipolar pacing, the threshold voltage needed to achieve capture in the atrium 134 is around 0.6 Volts. Using the atrial electrode 136 and the defibrillation electrode 150, a threshold voltage of 0.6 Volts is also sufficient to achieve capture in the atrium 134. Hence, using the atrial tip electrode 136 and the defibrillation electrode 150 for bipolar pacing, a substantially similar threshold voltage is sufficient to achieve capture as that applied when using conventional atrial bipolar pacing in the atrium 134. Hence, with the atrial tip electrode 136 and the defibrillation electrode 150, no greater voltage threshold is needed to achieve capture in the atrium 134.

Additionally, using an atrial ring electrode 510 and a defibrillation electrode 550 (FIG. 3), capture in the heart 28 is achieved. As shown in FIG. 6, a threshold voltage of 3.5 Volts is needed to achieve capture in the atrium 134. Moreover, a threshold voltage of 6.0 Volts is needed to achieve capture in the ventricle 190. The difference in threshold voltages (6.0−3.5=2.5 Volts) for these measurements is not as large as that when using the atrial tip electrode 136 and the defibrillation electrode (~10−0.6=9.4 Volts). Nevertheless, achieving capture in a desired chamber in the heart 28 is still possible.

Figure 4:
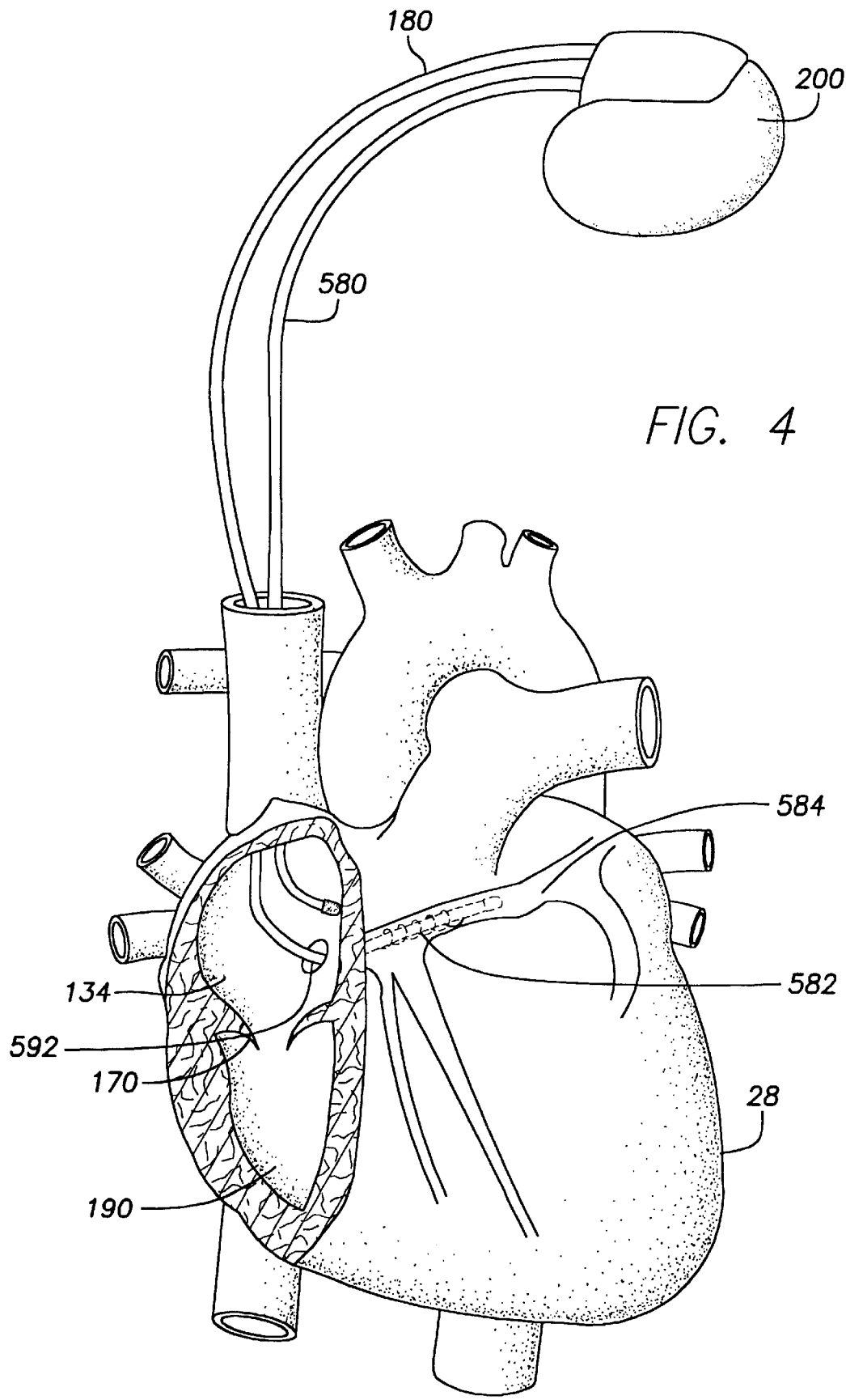
FIG. 4 is a partial cross-sectional view of a human heart showing an alternate embodiment of the lead system having the defibrillation electrode positioned in the coronary sinus.

An alternate embodiment of the present invention, as illustrated in FIG. 4, shows a lead system 570 having a unipolar lead 180 and a coronary sinus lead 580. The lead 180 terminates in a tip electrode 136 that is in contact with the atrial wall. The lead 580 terminates in the defibrillation electrode 582 that is adapted for placement into the coronary sinus 584. Accordingly, atrial pacing and sensing may be achieved between the atrial tip electrode 136 and the defibrillation electrode 582.

Figure 5:
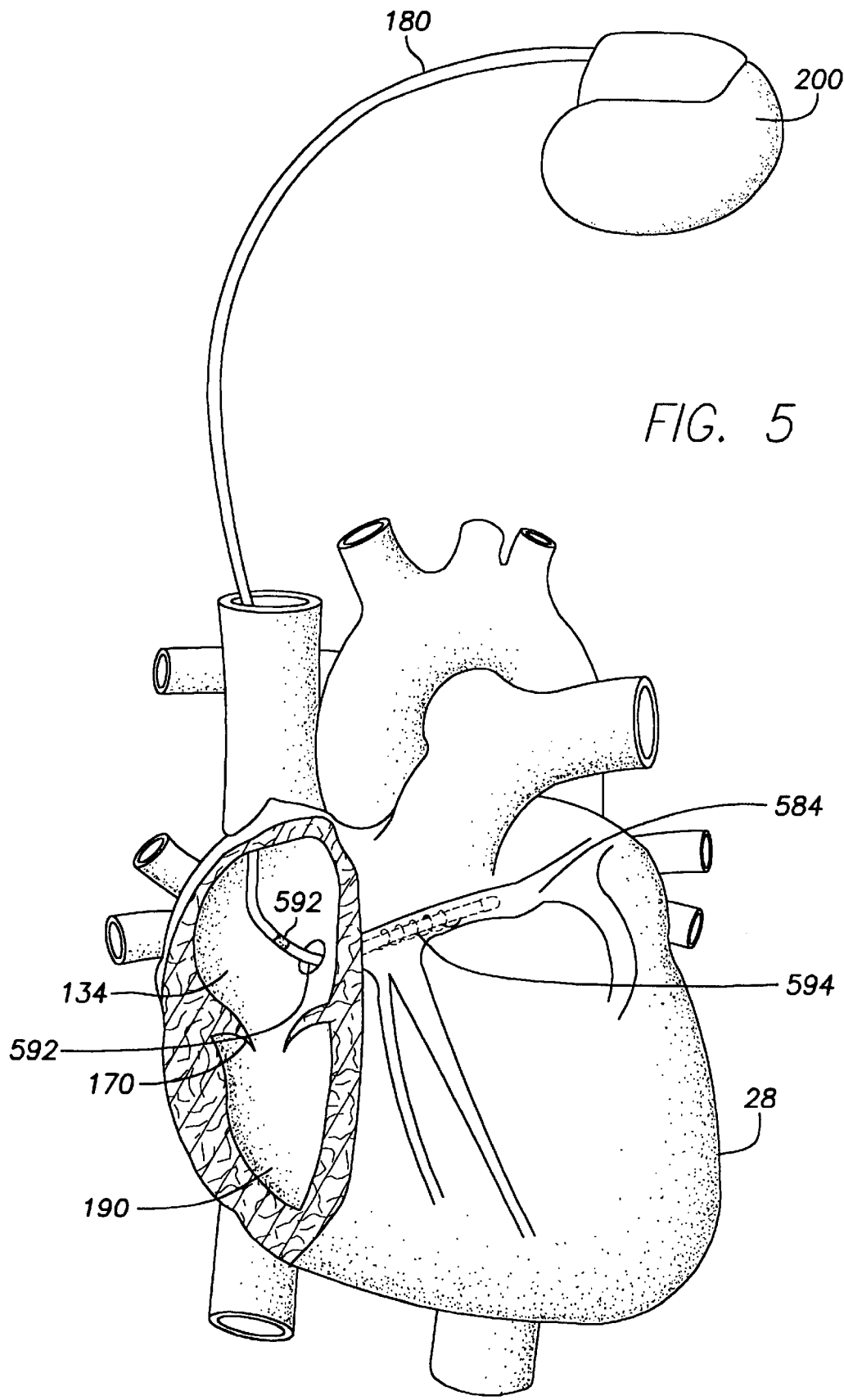
FIG. 5 is a partial cross-sectional view of a human heart showing an alternate embodiment of the lead system with a ring electrode in the atrium and a defibrillation electrode in the coronary sinus.

A still further embodiment of the present invention, as illustrated in FIG. 5, shows a single-pass lead 590 that includes a ring electrode 592 for placement in the atrium and a defibrillation electrode 594 adapted for placement in the coronary sinus 584. Accordingly, atrial pacing and sensing may be achieved between the ring electrode 592 and the defibrillation electrode 594.

Test results were obtained using the atrial tip electrode 136 and the ventricular defibrillation electrode 150 in atrial bipolar sensing. These test results show a significant improvement over the use of the atrial tip electrode 136 and the ventricular tip electrode 130 in atrial bipolar sensing. FIG. 7 illustrates a second table summarizing test results for various sensing lead configurations employed to sense intrinsic cardiac signals. The first column 710 indicates the lead configuration used in obtaining a particular measurement. The second column 720 indicates which electrode is used as an anode for the particular measurement. The third column 730 indicates the voltage level of the measured signal for the P-wave in millivolts (mV). The fourth column 740 indicates the voltage level of the measured signal for the R-wave in mV.

As shown in FIG. 7, using the atrial tip electrode 136 and the ventricular tip electrode 130 to sense intrinsic cardiac signals, the voltage level of the P-wave is 8.0 mV and that of the R-wave is 25.0 mV. Accordingly, the relative ratio of amplitudes of the R-wave and P-wave (R-wave/P-wave= 25.0/8.0) is 3.125. On the other hand, using the atrial tip electrode 136 and the defibrillation electrode 150, the voltage level of the P-wave is 8.0 mV and that of the R-wave is 11.0 mV. Accordingly, the relative ratio of amplitudes of the R-wave and P-wave is 1.375 (i.e., 11.0/8.0). In view of an already strong ventricular signals (R-wave), a lower R-wave/P-wave ratio ensures the ability to discriminate between the two waves. Moreover, any small variations in the P-wave are more detectable with a greater voltage range. Hence, the configuration of the atrial tip electrode 136 and the defibrillation electrode 150 provides superior results with respect to the relative amplitudes of the R-wave and P-wave in sensing intrinsic cardiac signals.

Moreover, using the atrial ring electrode 510 and ventricular tip electrode 530 (FIG. 3) to sense intrinsic cardiac signals, the voltage level of the P-wave is 1.5 mV and that of the R-wave is 24.0 mV. Accordingly, the relative ratio of amplitudes of the R-wave and P-wave is 16 (i.e., 24.0/1.5). On the other hand, using the atrial ring electrode 510 and defibrillation electrode 550 (FIG. 3), the voltage level of the P-wave is 1.7 mV and that of the R-wave is 12.0 mV. Accordingly, the relative ratio of amplitudes of the R-wave and P-wave is 7.1 (12.0/1.7). Hence, the configuration of the atrial tip electrode 136 and the defibrillation electrode 150 provides significantly improved results with respect to the relative amplitudes of the R-wave and P-wave when sensing intrinsic cardiac signals.

In view of the foregoing, it will be appreciated that the invention overcomes the long-standing need for a system and method for using an atrial unipolar lead to effectively perform bipolar sensing and pacing in the atrium 134 of the heart 28. The invention provides a lead system which provides improved performance results over those of standard combipolar lead systems. The invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which fall within the meaning and range of equivalency of the claims are to be embraced within their scope.

What is claimed is:

1. A cardiac system for use in performing bipolar pacing in an atrium of the heart, the system comprising:
    an atrial electrode configured for placement in the atrium;
    a ventricular electrode configured for placement in the ventricle and having a surface area greater than about 60 mm$^2$; and
    a pulse generator that is configured to generate stimulation pacing pulses and to deliver the stimulation pacing pulses between the atrial electrode and the ventricular electrode.

2. The system, as defined in claim 1, wherein the atrial electrode comprises a cathode electrode and the ventricular electrode comprises an anode electrode.

3. The system, as defined in claim 1, wherein the ventricular electrode comprises a shocking coil which delivers defibrillation pulses to the ventricle.

4. The system, as defined in claim 1, wherein the system further comprises a single cable containing respective leads for the atrial electrode and the ventricular electrode.

5. The system, as defined in claim 1, wherein the atrial electrode comprises a tip electrode adapted for placement in contact with the atrial wall.

6. The system, as defined in claim 1, wherein the atrial electrode comprises a ring electrode.

7. The system, as defined in claim 6, wherein the ring electrode is adapted for placement in close proximity to the atrial wall.

8. The system, as defined in claim 6, wherein the ring electrode is incorporated with a lead for the ventricular electrode.

9. A cardiac system adapted to provide stimulation pacing pulses and defibrillation shocks and to perform bipolar pacing in an atrium of the heart, the system comprising:
    an atrial electrode configured for placement in the atrium, and electrically connectable to the cardiac device;
    a defibrillation electrode configured for placement in the ventricle, and electrically connectable to the cardiac device; and
    a pulse generator that is configured to generate stimulation pacing pulses and to deliver the stimulation pacing pulses between the atrial electrode and the defibrillation electrode.

10. The system, as defined in claim 9, wherein the system further comprises a single cable containing respective leads for the atrial electrode and the defibrillation electrode.

11. The system, as defined in claim 9, wherein the atrial electrode comprises a tip electrode placed in contact with the atrial wall.

12. The system, as defined in claim 9, wherein the atrial electrode comprises a ring electrode.

* * * * *